United States Patent [19]

Sherman

[11] Patent Number: 5,998,365

[45] Date of Patent: Dec. 7, 1999

[54] MICROEMULSION PRECONCENTRATES COMPRISING CYCLOSPORINS

[75] Inventor: Bernard Charles Sherman, Willowdale, Canada

[73] Assignee: Bernard C. Sherman, Weston, Canada

[21] Appl. No.: 09/077,803

[22] PCT Filed: Dec. 3, 1996

[86] PCT No.: PCT/CA96/00803

§ 371 Date: Jun. 15, 1998

§ 102(e) Date: Jun. 15, 1998

[87] PCT Pub. No.: WO97/22358

PCT Pub. Date: Jun. 26, 1997

[30] Foreign Application Priority Data

Dec. 15, 1995 [NZ] New Zealand ........................ 280689

[51] Int. Cl.$^6$ ............... A61K 38/00; A61K 38/13
[52] U.S. Cl. ............... 514/11; 514/885; 514/937; 514/938; 514/963; 514/964; 514/970; 424/455; 424/489
[58] Field of Search ................ 514/11, 885, 937, 514/938, 963, 964, 970; 424/455, 489

[56] References Cited

U.S. PATENT DOCUMENTS 5,342,625  8/1994  Hauer et al. ........................ 424/455

FOREIGN PATENT DOCUMENTS

| 0 589 843 | 3/1994 | European Pat. Off. . |
| 0 712 631 | 5/1996 | European Pat. Off. . |
| 2 636 534 | 3/1990 | France . |
| 2 282 586 | 4/1995 | United Kingdom . |
| WO 95/11039 | 4/1995 | WIPO . |
| WO 96/13273 | 5/1996 | WIPO . |
| WO 96/36316 | 11/1996 | WIPO . |

*Primary Examiner*—F. T. Moezie
*Attorney, Agent, or Firm*—Nixon & Vanderhye P.C.

[57] ABSTRACT

A pharmaceutical composition in the form of a microemulsion preconcentrate comprising a cyclosporin dissolved in a solvent system further comprising a hydrophobic component, a hydrophilic component, and a surfactant, wherein either the hydrophobic component is selected from tocol, tocopherols, tocotrienols, and derivatives thereof, or the hydrophilic component is selected from propylene carbonate or polyethylene glycol having an average molecular weight of less than 1000.

14 Claims, No Drawings

MICROEMULSION PRECONCENTRATES COMPRISING CYCLOSPORINS

This application represents the national phase of PCT/CA96/00803, filed Dec. 3, 1996.

TECHNICAL FIELD

The invention is directed to pharmaceutical compositions which facilitate the administration of cyclosporins.

BACKGROUND ART

The term "cyclosporins" as used herein shall mean the class of nonpolar polypeptides. as defined in the Merck Index, Eleventh Edition. One such cyclosporin is cyclosporin A, also known as "cyclosporine" and hereinafter referred to as "cyclosporine", known to be therapeutically active as an immunosuppressant.

The term "composition" as used herein is to be understood as meaning any composition containing a drug along with inactive ingredients that are pharmaceutically acceptable by reason of not being excessively toxic in the quantities required.

The term "solvent system" as used herein is to be understood to mean the material in which the drug (i.e. a cyclosporin) is dissolved. The solvent system may be a single solvent or a combination or mixture of ingredients included as solvents, surfactants, diluents or for other purposes.

Cyclosporins are hydrophobic and have low solubility in aqueous media. This makes it difficult to design pharmaceutical compositions which exhibit satisfactory absorption into systemic circulation after oral administration, or absorption into the target tissue upon topical administration.

The cyclosporin can be dissolved in an organic solvent (e.g. ethanol or propylene glycol), but if the solvent is water-miscible, when the composition is mixed with gastrointestinal fluid or other aqueous media the cyclosporin will precipitate.

Various methods of overcoming this problem are known in the prior art, but all have certain limitations.

U.S. Pat. No. 4,388,307 discloses compositions comprising cyclosporine in an emulsion preconcentrate that is not water-miscible, but forms an emulsion upon being mixed into gastrointestinal fluids. A commercial product that has been sold under the trademark "Sandimmune" is made according to U.S. Pat. No. 4,388,307, and, more specifically, comprises cyclosporine dissolved in a solvent system comprising ethanol, a vegetable oil and a surfactant. Although this composition was superior to previously known compositions, it still exhibits absorption that is less than the maximum possible and is variable. Also, the use of ethanol has disadvantages, as ethanol is volatile, and the capsules of Sandimmune must be individually packaged in metallic pouches to avoid loss of ethanol by evaporation.

U.S. Pat. No. 5,342,625 discloses compositions that are said to be superior in certain respects to the compositions of U.S. Pat. No. 4,388,307. The compositions of U.S. Pat. No. 5,342,625 comprise, in addition to the cyclosporin, a hydrophilic phase, a lipophilic (i.e. hydrophobic) phase and a surfactant. The hydrophilic phase is either propylene glycol or a pharmaceutically acceptable alkyl or tetrahydrofurfuryl di- or partial-ether of a low molecular weight mono- or poly-oxy-alkanediol.

The lipophilic phase comprises a solvent which is non-miscible with the hydrophilic phase. and is preferably a fatty acid triglyceride.

It is disclosed that compositions according to U.S. Pat. No. 5,342,625, when added to water, disperse into emulsions with droplet size of less than 2000 Å, which is smaller than obtained with prior art compositions, thus leading to improved absorption.

Emulsions with droplet size of less than 2000 Å are defined as "microemulsions". Compositions that, upon addition to water, disperse into microemulsions are called "microemulsion preconcentrates".

A composition made according to the disclosure of U.S. Pat. No. 5,342,625 is now marketed under the trademark "Neoral", in the form of both a soft gelatin capsule which encloses the microemulsion preconcentrate and an oral liquid which is a microemulsion preconcentrate intended to be diluted into an aqueous drink before ingestion.

For both the soft gelatin capsules and the oral liquid, the labelling indicates that the "Neoral" emulsion preconcentrate comprises cyclosporine dissolved in ethanol and propylene glycol as hydrophilic solvents, corn oil as lipophilic (hydrophobic) solvent, and polyoxyl 40 hydrogzenated castor oil as surfactant. It also contains dl-alpha-tocopherol at a level of about one percent by weight as antioxidant, apparently to prevent oxidation of the corn oil.

While "Neoral" does enable improved absorption relative to Sandimmune, it still has certain undesirable properties. Specifically:

1 Ethanol is volatile, so that the soft gelatin capsules have to be packaged individually in metallic pouches to prevent evaporation of the ethanol.
2. The meiting point of the microemulsion preconcentrate is about 20° C. so that it may solidify at room temperature. This means that the oral solution may have to be warmed and melted to be dispensed. Also it cannot be mixed with a cold aqueous drink and is limited to being mixed into warn aqueous drinks.
3. Ethanol contributes to an undesirable taste of the microemulsion preconcentrate, so that, even after dilution into a sweetened drink, there is still a somewhat unpleasant taste.
4. The concentration of cvciosporine is limited to about 100 mg per mL so that a soft gelatin capsules containing 100 mg of cyclosporine is larger than desirable and difficult to swallow.

International Publication Number WO 94/25068 discloses improved compositions in the form of microemulsion preconcentrates in which the principal solvent for the cyclosporin is an alcohol which is selected from alcohols having a boiling point above 100° C. and a solubility in water of under 10 g per 100 g at 20° C. Such alcohols are referred to as a hydrophobic alcohols.

It is disclosed that a hydrophobic alcohol can be used in place of the combination of hydrophilic and hydrophobic solvents.

Preferred hydrophobic alcohols. within the scope of the disclosure of WO 94/25068. are saturated alkyl alcohols having 8 to 14 carbon atoms per molecule, including 1-octyl, 2-octyl, 1-decyl, 1-dodecyl and 1-tetradecyl alcohols.

Compositions according to the disclosure of WO 94/25068 overcome some of the problems of prior art compositions. However, the hydrophobic alcohols have a foul taste so that, even after dilution into a sweetened aqueous drink, there is still an unpleasant taste.

In view of the difficulties with prior art compositions, the object of the invention is to enable microemulsion preconcentrates comprising cyclosporins which use combinations of excidients (i.e. inactive ingredients) not disclosed in the prior art, and thereby overcome some or all of the problems encountered with prior art compositions.

SUMMARY OF THE INVENTION

As with compositions of U.S. Pat. No. 5,342,625, compositions of the within invention take the form of microemulsion preconcentrates comprising a cyclosporin dissolved in a solvent system further comprising at least one hydrophobic solvent, at least one hydrophilic solvent and at least one surfactant.

For purposes of the present disclosure and claims, the term "hydrophobic" will be taken as meaning being insoluble in water or substantially insoluble in water, i.e. having a solubility of less than 1 part per 1000 parts of water by weight at 20° C., and the term "hydrophilic" will be taken as meaning miscible with water or having a solubility of more than 1 part per 100 parts of water by weight at 20° C.

One feature of the present invention is to use, as hydrophobic solvent, an ingredient selected from tocol, tocopherols, tocotrienols, and derivatives thereof.

Another feature of the within invention is to use, as hydrophilic solvent, solvents other than those disclosed in U.S. Pat. No. 5,342,625 and in particular a solvent selected from propylene carbonate and polyethylene glycols having average molecular weight of less than 1000.

More particularly the invention is a pharmaceutical composition in the form of a microemulsion preconcentrate comprising a cyclosporin dissolved in a solvent system further comprising a hydrophobic component, a hydrophilic component and a surfactant, wherein either:

1) the hydrophobic component is selected from tocol, tocopherols and tocotrienols, and derivatives thereof, and comprises at least about two percent of the composition by weight, or 2) the hydrophilic component is propylene carbonate or polyethylene glycol having average molecular weight of less than 1000.

DETAILED DESCRIPTION OF THE INVENTION

A microemulsion preconcentrate comprising a cyclosporin must contain a hydrophobic solvent and surfactant.

A hydrophobic solvent is needed, because if the cyclosporin is dissolved in only a hydrophilic solvent, then when the composition is mixed with a aqueous medium, the hydrophilic solvent will dissolve in the water, causing precipitation of the cyclosporin.

It is also necessary that the solvents used in the composition have adequate capacity to dissolve the cyclosporin and to keep it dissolved without precipitation.

As aforesaid, International Patent Number WO 94/25068 discloses use of hydrophobic alcohols as solvents, and such alcohols, being both hydrophobic and having adequate solvent capacity for cyclosporins, can render it unnecessary to use a hydrophilic solvent as cosolvent. However, when the hydrophobic solvent is not an alcohol, it appears to be necessary to use as cosolvent a hydrophilic solvent that is a good solvent for the cyclosporins.

In U.S. Pat. No. 5,342,625, the only hydrophobic solvents that are disclosed are fatty acid triglycerides, and it is stated that especially suitable are neutral oils, e.g. neutral plant oils.

As aforesaid, one feature of the within invention is to use, as hydrophobic solvent, an ingredient selected from tocol, tocopherols and tocotrienols, and derivatives thereof.

The term "tocopherols" as used herein is to be understood to mean any one of or a mixture of any of the compounds which can be regarded as a substituted tocol and is identified as a type of tocopherol in the Merck Index Eleventh Edition at entry numbers 9417 to 9423 inclusive and entry number 9832, specifically including alpha-, beta-, delta- and garmma-tocopherol.

Alpha-tocopherol is also known as Vitamin E.

The term "tocotrienol" as used herein shall be understood to mean any one of or a mixture of alpha-, beta-, delta- and gamma-tocotrienol. Tocotrienols are similar to tocopherols but have an unsaturated side chain consisting of three double bonds.

The term "derivative" will be understood to mean any compound that can be formed by a reaction with any compound selected from tocol, tocopherols and tocotrienols. Derivatives will thus include, for example, tocol acetate, and alpha-tocopherol acetate.

Some or all of tocol, the tocopherols and the tocotrienols, and derivatives thereof are available as different steroisomers, and it will be understood that the different stereoisomer or mixtures thereof are included within the definition.

Preferred as hydrophobic solvents are alpha-tocopherol, alpha-tocopherol acetate, and natural mixed tocopherols.

Especially preferred is natural mixed tocopherols. These are available, for example, as products sold under the tradenames Tenox GT-2 by Eastman Chemical Products Inc. and Coviox T70 by Henkel Corporation.

Tenox GT-2 and Coviox T70 both are comprised of about 70% total tocopherols and 30% vegetable oil. The total tocopherol content in these products is made up of approximately 12% to 14% d-alpha, 62% to 65% d-gamma, 23$ to 24% d-delta and 1% d-beta.

The minimum effective amount of the hydrophobic solvent selected from tocol, tocopherols and tocotrienols, and derivatives thereof is about two per cent of the total composition by weight. The amount will preferably be at least four percent of the composition by weight, and most preferably from about eight percent to about twenty-five percent.

As aforesaid, a second feature of the present invention is to use, as hydrophilic solvent, solvents other than those disclosed in U.S. Pat. No. 5,342,625, and in particular, a solvent selected from propylene carbonate and polyethylene glycols having average molecular weight of less than 1000.

The hydrophilic solvents used in the prior art have exhibited several problems including the following:

1. They may be excessively volatile so that a capsule containing the composition must be packed in metallic foil to prevent evaporation.
2. They may exhibit foul taste.
3. They may be excessively hydrophilic so that when the composition is mixed with water they tend to be extracted from the composition causing, some precipitation of the cyclosporin.
4. The melting points of compositions using such solvents may not be low enough to enable the compositions to be dispersed in cold aqueous drinks.

It has been found that some or all of these problems can be overcome by selecting a hydrophilic solvent from among propylene carbonate and polyethylene glycols having an average molecular weight of less than 1000. Particularly preferred are propylene carbonate and polyethylene glycols having average molecular weight from about 200 to about 400. Most preferred is propylene carbonate.

While the two features of the invention mav be used independently of each other, it is especially preferred to use them together. Especially preferred compositions are thus compositions which comprise both a hydrophobic solvent selected from tocol, tocopherols and tocotrienols, and derivatives thereof and a hydrophilic solvent selected from propylene carbonate and polyethylene glycols having an average molecular weight of less than 1000.

Compositions of the within invention will comprise, in addition to the cyclosporin, a hydrophobic solvent, and a hydrophilic solvent, at least one surfactant.

Examples of suitable surfactants are:

i) Reaction products of natural or hydrogenated vegetable oils and ethylene glycol; i.e., polyoxyethylene glycolated natural or hydrogenated vegetable oils; for example polyoxyethylene glycolated natural or hydrogenated castor oils. Particularly suitable are the products designated in the United States Pharmacopoeia and National Formulary as Polyoxyl 35 Castor Oil and Polyoxyl 40 Hydrogenated Castor Oil, which are available under the trade names Cremophor EL and Cremophor RH40 respectively. Also suitable for use in this category are the various tensides available under the trade names Nikkol, e.g. Nikkol HCO-60. Nikkol HCO-60 is a reaction product of hydrogenated castor oil and ethylene oxide.

ii) Polyoxyethylene-sorbitan-fatty acid esters; e.g. mono- and tri-lauryl, palmityl, stearyl and oleyl esters: e.g. products of the type known as polysorbates and commercially available under the trade name "Tween".

iii) Polyoxyethylene fatty acid esters: for example, polyoxyethylene stearic acid esters of the type known and commercially available under the trade name Myrj as well as polyoxyethylene fatty acid esters known and commercially available under the trade name "Cetiol HE".

iv) Polyoxyethylene-polyoxypropylene co-polymers, e.g. of the type known and commercially available under the trade names "Pluronic" and "Emkalyx".

v) Polyoxyethylene-polyoxypropylene block co-polymers, e.g. of the type known and commercially available under the trade name "Poloxamer".

vi) Dioctylsuccinate, dioctylsodiumsulfosuccinate, di-[2-ethylhexyl]-succinate or sodium lauryl sulfate.

vii) Phospholipids, in particular lecithins.

viii) Propylene glycol mono- and di-fatty acid esters such as propylene glycol dicaprylate, propylene glycol dilaurate, propylene glycol hydroxystearate, propylene glycol isostearate, propylene glycol laurate, propylene glycol ricinoleate, propylene glycol stearate and so forth.

ix) Bile salts; e.g. alkali metal salts, for example sodium taurocholate.

x) Trans-esterification products of natural vegetable oil triglycerides and polyalkylene polyols; e.g. of the type known and commercially available under the trade name Labrafil M1944CS.

xi) Mono-, di- and mono/di-glycerides, especially esterification products of caprylic or capric acid with glycerol.

xii) Sorbitan fatty acid esters; for example, of the type known and commercially available under the trade name Span.

xiii) Pentaerythritol fatty acid esters and polyalkylene glycol ethers; for example pentaerythrite-dioleate, -distearate, -monolaurate, -polyglycol ether and -monostearate as well as pentaerythrite-fatty acid esters.

xiv) Monoglycerides; e.g. glycerol monooleate, glycerol monopalmitate and glycerol monostearate; for example as known and commercially available under the trade names Myvatex, Myvaplex and Myverol, and acetylated, e.g. mono- and di-acetylated mono-glycerides; for example as known and commercially available under the trade name Myvacet.

xv) Glycerol triacetate or 1,2,3)-triacetin; and xvi) Sterols and derivatives thereof, for example cholesterols and derivatives thereof, in particular phytosterols; e.g. products comprising sitosterol, campesterol or stigmasterol, and ethylene oxide adducts thereof, for examples soya sterols and derivatives thereof, such as known under the trade name Generol.

Suitable surfactants will not necessarily be limited to those listed above, but will be understood to include any compound which causes the composition to be more easily dispersible in water.

Preferred surfactants are reaction products of natural or hydrogenated vegetable oils and ethylene glycol; i.e. polyoxethylene glycolated natural or hydrogenated vegetable oils.

Especially preferred surfactants are polyoxyethylene glycolated natural or hydrogenated castor oils including those designated in the United States Pharmacopoeia and National Formulary as Polyoxyl 35 Castor Oil and Polyoxyl 40 Hydrogenated Castor Oil.

It will be understood that not all surfactants will act equally well with all solvents to improve dispersion in water. Determination of suitable combinations of hydrophobic solvent, hydrophilic solvent and surfactant for particular applications within the scope of the invention will be within the capability of persons skilled in the art of product formulation.

Compositions in accordance with the invention may contain other ingredients in addition to the drug, one or more hydrophobic solvents, one or more hydrophilic solvents and one or more surfactants.

For example, the composition may include, in addition to the foregoing, one or more other ingredients that are included as diluents.

A composition in accordance with the invention may also contain, for example, a thickening agent (i.e. viscosity increasing agent). Suitable thickening agents may be any of those known and emploved in art, including, for example, pharmaceutically acceptable polymeric materials and inorganic thickening agents. However, where oral administration is intended, the use of thickening agents as aforesaid will generally not be required. Lose of thickeningy agents is, on the other hand, indicated. e.g. where topical application is foreseen.

Compositions in accordance with the invention may also include one or more further ingredients: such as antioxidants, flavouring agents and so forth.

Compositions in accordance with the invention may be liquids at ambient temperature or they may be solids prepared, for example, by use of a hydrophobic solvent or surfactant with melting point above ambient temperature. The ingredients may be blended at a temperature above the melting, point and then used to fill capsules while still molten, or cooled to form solids. The solids may be ground into granules or powder for further processing; for example, filling capsules or manufacture of tablets.

If it is desired to increase the melting point to ensure that the composition is a solid at room temperature, this may be accomplished by adding a further ingredient with a relatively high melting point such as, for example, polyethylene glycol with average molecular weight of above 1000.

Capsules or tablets may be further processed by applying coatings thereto.

Especially where oral administration is contemplated, compositions in accordance with the invention may comprise end dosage forms for administration as microemulsion preconcentrates. For example the microemulsion preconcentrate may be directly used as liquid for oral ingestion, parenteral use, or topical application or it may be encapsulated into gelatin capsules for oral ingestion.

However, the present invention also provides pharmaceutical compositions in which the microemulsion preconcentrate is further processed into a microemulsion. Thus where oral admniistration is practised, microemulsions obtained, e.g. by diluting a microemulsion preconcentrate with water or other aqueous medium (for example, a sweetened or flavoured preparation for drinking), may be employed as formulations for drinking. Similarly, where topical application is foreseen, compositions comprising a microemulsion preconcentrate, a thickening agent and water will provide an aqueous microemulsion in gel, paste, cream or like form.

Compositions in accordance with the present invention, whether microemulsion preconcentrates or microemulsions, may be employed for administration in any appropriate manner and form; e.g. orally, as liquids or granules or in unit dosage form, for example in hard or soft gelatin encapsulated form, parenterally or topically; e.g. for application to the skin; for example in the form of a cream, paste, lotion, gel, ointmient, poultice, cataplasm, plaster, dermal patch, powder, topically applicable spray, or the like, or for ophthalmic application; for example in the form of an eye-drop, lotion or gel formulation. Readily flowable forms may also be employed; e.g. for intralesional injection for the treatment of psoriasis, or may be administered rectally. Compositions in accordance with the invention are, however, primarily intended for oral or topical application, including application to the skin or eyes.

The relative proportion of the cyclosporin and other ingredients in the compositions of the invention will, of course, vary considerably depending on the particular type of composition concerned; e.g,. whether it is a microemulsion preconcentrate or microemulsion, the route of administration, and so forth. The relative proportions will also vary depending on the particular ingredients employed and the desired physical characteristics of the composition, e.g. in the case of a composition for topical use, whether this is to be a free flowing liquid or a paste. Determination of workable proportions in any particular instance will generally be within the capability of persons skilled in the art. All indicated proportions described herein are accordingly to be understood as being examples and not as not limiting the invention in its broadest aspect.

Compositions for topical use suitably comprise one or more carriers or diluents and/or other ingredients (e.g. thickening agents, emulsifying agents. preserving agents, moisturizing agents, colourants and so forth) providing a suitable carrier.

Selection of excipients for the preparation of such formulations will, of course, be determined by the type of formulation desired as well as the particular condition to be treated, the area to be treated, and the effect desired. Some conditions will more suitably be treated with hydrophobic, e.g. fat-based compositions, for example compositions in accordance with the invention comprising a petrolatum based ointment or cream as carrier medium. In contrast, compositions for use in the treatment of some conditions will more appropriately be treated with more hydrophilic compositions.

By use of suitable individual carrier ingredients or mixtures thereof, compositions may be obtained in liquid or semi-solid form.

The invention will be more fully understood by the following examples which are illustrative but not limiting of compositions in accordance with the present invention.

EXAMPLES

In each of the following examples the ingredients by weight were placed in a container in the proportions shown, after the polyoxyl 40 hydrogenated castor oil was liquified by warming it to above 30° C.

Example 1

| | |
|---|---|
| cyclosporine | 1.0 |
| ethanol | 0.8 |
| dl-alpha-tocopherol acetate | 1.2 |
| polyoxyl 40 hydrogenated castor oil | 7.0 |
| | 10.0 |

Example 2

| | |
|---|---|
| cyclosporine | 1.0 |
| benzyl alcohol | 0.5 |
| polyethylene glycol 300 | 2.0 |
| di-alpha-tocopherol acetate | 1.0 |
| polyoxyl 40 hydrogenated castor oil | 5.5 |
| | 10.0 |

Example 3

| | |
|---|---|
| cyclosporine | 1.0 |
| ethanol | 0.8 |
| dl-alpha-tocopherol | 1.2 |
| polyoxyl 40 hydrogenated castor oil | 7.0 |
| | 10.0 |

Example 4

| | |
|---|---|
| cyclosporine | 1.0 |
| propylene carbonate | 2.5 |
| dl-alpha-tocopherol | 1.5 |
| polyoxyl 40 hydrogenated castor oil | 5.0 |
| | 10.0 |

Example 5

| | |
|---|---|
| cyclosporine | 1.0 |
| propylene carbonate | 2.0 |
| dl-alpha-tocopherol | 2.0 |
| polyoxyl 40 hydrogenated castor oil | 5.0 |
| | 10.0 |

Example 6

| | |
|---|---|
| cyclosporine | 1.0 |
| propylene carbonate | 3.0 |
| Coviox T70 | 1.5 |
| polyoxyl 40 hydrogenated castor oil | 5.4 |
| | 10.9 |

In the case of all of examples 1 to 6, upon blending and heating a clear liquid was formed.

In the case of each of examples 1 to 6, when a quantity of the composition was added to water and upon shaking, the composition dispersed to form a microemulsion.

The composition of each of examples 1 to 6 is a microemulsion preconcentrate directly useable as drops for oral ingestion or as a liquid for opthalmic or topical use. Alternatively, these compositions may be further processed in various ways previously described, including, for example, their incorporation into gelatin capsules or tablets for oral ingestion, or into microemulsions and various other forms for oral or topical use.

For example, they may be mixed into water or other aqueous media and used as a drink. Alternatively, they may be incorporated into a cream, ointment, gel or the like by combination with further additives, e.g., thickening agents, paraffins, etc. as hereinbefore described.

In the case of each of examples 4.5 and 6, the melting point of the composition is well below 20° C., so that these compositions are especially well suited for use as preconcentrates to be added to an aqueous medium and used as a drink, regardless of whether the drink is warm or cold.

INDUSTRIAL APPLICABILITY

From the foregoing description it will be apparent that in the present invention there is provided an improved pharmaceutical composition which permits the more efficient administration and absorption of cyclosporins.

What is claimed:

1. A pharmaceutical composition wherein said composition is a microemulsion preconcentrate comprising a cyclosporin dissolved in a solvent system, said solvent system comprising a hydrophilic component, a hydrophobic component, and a surfactant, wherein the hydrophilic component is propylene carbonate or polyethylene glycol having average molecular weight of less than 1000.

2. A pharmaceutical composition according to claim 1 wherein the hydrophilic component is propylene carbonate.

3. A pharmaceutical composition according to claim 1 wherein the hydrophilic component is polyethylene glycol having average molecular weight of less than 1000.

4. A pharmaceutical composition according to claim 1 wherein the hydrophilic component is polyethylene glycol having average molecular weight of not more than 600.

5. A pharmaceutical composition according to claim 1 wherein the hydrophobic component is selected from the group consisting of tocol, a tocol derivative, a tocopherol, a tocopherol derivative, a tocotrienol and a tocotrienol derivative wherein said hydrophobic component comprises at least two percent of the composition by weight.

6. A composition according to claim 5 wherein the hydrophobic component constitutes at least four percent of the composition by weight.

7. A composition according to claim 6 wherein the hydrophobic component constitutes at least eight percent of the composition by weight.

8. A composition according to claim 5 wherein the hydrophobic component is selected from the group consisting of tocopherol and a tocopherol derivative.

9. A composition according to claim 8 wherein the hydrophobic component is vitamin E or vitamin E acetate.

10. A composition according to claim 8 wherein the hydrophobic component is natural mixed tocopherols.

11. A composition according to claim 1 wherein the cyclosporin is cyclosporine.

12. A composition according to claim 1 wherein the surfactant comprises a polyoxyethylene glycolated natural or hydrogenated vegetable oil.

13. A composition according to claim 1 suitable for oral administration.

14. A composition according to claim 1 comprising from 5 to 20% by weight of cyclosporin.

* * * * *